United States Patent [19]

Iyengar et al.

[11] Patent Number: 5,051,271

[45] Date of Patent: Sep. 24, 1991

[54] STARCH-DERIVED, FOOD-GRADE, INSOLUBLE BULKING AGENT

[75] Inventors: Radha Iyengar, Belmont; Aleksey Zaks, Brookline; Akiva Gross, Newton, all of Mass.

[73] Assignee: Opta Food Ingredients, Inc., Cambridge, Mass.

[21] Appl. No.: 440,585

[22] Filed: Nov. 22, 1989

[51] Int. Cl.$^5$ .......................................... A23L 1/0522
[52] U.S. Cl. ..................... 426/658; 426/804; 426/661; 426/613; 426/660; 426/565; 426/659; 426/603
[58] Field of Search ............... 426/578, 658, 804, 573, 426/661, 660, 659, 603, 565, 613

[56] References Cited

U.S. PATENT DOCUMENTS

| | | | |
|---|---|---|---|
| 3,730,840 | 6/1973 | Sugimoto et al. | 195/31 |
| 3,766,011 | 4/1973 | Kurimoto et al. | 195/31 |
| 4,303,294 | 12/1981 | Rispoli et al. | 426/578 |
| 4,510,166 | 4/1985 | Lenchin | 426/578 |
| 4,726,957 | 2/1988 | Lacourse | 426/578 |
| 4,810,518 | 3/1989 | Haisman et al. | 426/578 |
| 4,956,193 | 9/1990 | Cain et al. | 426/578 |

OTHER PUBLICATIONS

D. Sievert and Y. Pomeranz, *Cereal Chem.*, 66(4):342–347 (1989).

H. N. Englyst et al., *Am. J. Clin. Nutrition*, 46:873–874 (1987).

*Primary Examiner*—Jeanette Hunter
*Attorney, Agent, or Firm*—Hamilton, Brook, Smith & Reynolds

[57] ABSTRACT

A method for preparing a food grade, insoluble bulking agent from starch is disclosed. The method involves a retrogradation process followed by enzymatic hydrolysis to form a modified starch product which can be used as a filler or as a bulking or texturizing agent in low-fat food formulations.

10 Claims, No Drawings

STARCH-DERIVED, FOOD-GRADE, INSOLUBLE BULKING AGENT

BACKGROUND

Starch is one of the principle and most abundant carbohydrates. It is formed in plants as a result of photosynthesis and constitutes a source of energy for a variety of organisms including man. The world production of starch is estimated to be 18 million tons, about 50% of that amount is intended for use in foods where starch helps to improve the functional properties of products and provides a source of many oligosaccharides. Starch can also be used in many ways other than a foodstuff such as in glues, coatings sizings and flocculating agents chemicals and building materials.

The industrial use of starch is based on its unique chemical and physical characteristics. Starch can be used in a variety of different ways including as intact granules as swollen granules as a dispersion, as a film, or after conversion to a mixture of oligosaccharides.

Starches can be modified in various ways to render them more suitable for use in the food, paper, textile, soap, laundry cosmetic and pharmaceutical industries. Generally starch is modified by physical, chemical or enzymatic means to acquire particular properties. Physical modifications may be induced by mechanical forces, and/or by hydrothermal treatments that lead to partial or total reorganization of the granular structure. The nutritional and physical properties of physically-modified starch is different from those of the starting material. For example, the complete disorganization of the starch granular structure, which is insoluble in cold water, leads to a form of starch that is highly soluble in cold water. The degradation of amylose by shear leads to the formation of easily digestible oligosaccharides. C. Mercier, *Staerke*, 29:48 (1977). During thermal treatment of starches or during simple prolonged storage, a number of significant changes occurs that are usually described as "retrogradation". In general, retrogradation is a crystallization process that can be detected by X-ray diffraction. It is brought about by the strong tendency of starch hydroxy groups to form hydrogen bonds with adjacent starch molecules. The changes taking place during retrogradation have a major impact on texture and digestibility of starch-containing food products. Retrogradation is an important factor in the staling of bread and in the texture changes of most starch-containing foods.

Retrogradation of starches has been studied by a variety of techniques including X-ray diffraction, differential scanning calorimetry, and measurements of shear modules. M. J. Miles et al., *Carbohydrate Research*, 135:271 (1985.) A study of the structure of retrograded amylose revealed that it is composed of crystalline, double-helical regions that interlock with amorphous regions. The formation of crystalline regions increases the rigidity of the granules and reinforces the amylose matrix. The amorphous regions can be hydrolyzed by a number of acids and by enzymes such as alpha amylases, leaving the crystalline regions intact. Hence, retro gradation results in an overall increase in resistance of the starch to the hydrolysis by glucosidic enzymes. S. G. Ring. J. M. Gee M. Whittam, P. Orford and, I. T. Johnson, *Food Chemistry*, 28:97 1988.

Liquefaction (partial hydrolysis) and saccharification (conversion of liquified starch into glucose) of starch-containing materials by enzymes have become increasingly more important than traditional acid-catalyzed hydrolysis. Among other advantages, enzyme technology provides higher yields, significantly improves product quality and reduces energy consumption. Oligosaccharides Produced by enzymatic hydrolysis can be used in a variety of applications. For example, maltooligosaccharides produced from starch by hydrolysis with alpha amylase can be used in adhesives and in food applications such as syrups, flavor encapsulation., texture control, binding agents, and gels.

Despite a considerable effort directed towards the utilization of enzymes in the starch industry in recent years, there are still few enzyme-derived starch-based products on the market That is particularly evident in the area of low calorie foods. Until recently, starch was thought to be completely hydrolyzed and adsorbed from the small intestine of man. This assumption was based on the fact that the amount of amylase in the human pancreas exceeds the amount that is necessary for complete hydrolysis of the starch consumed. H. N. Englyst and G. T. Macfarlane, *J. Sci. Food Agric.*, 137:699 (1986). Physical modification of starch may result in a product that is resistant to digestion in the small intestine. S. G. Ring et al., *Food Chemistry*, 28:97 (1988). Thus the development of low-calorie starch-based products is now of considerable interest.

SUMMARY OF THE INVENTION

The invention relates to a food grade, non-digestible, low-calorie bulking agent derived from starch and a process for producing it. The process involves retrogradation of starch, followed by enzymatic or chemical hydrolysis to reduce or remove, the amorphous regions of the starch molecule. The modified starch produced by the process is a retrograded starch containing little or no amorphorus regions. The properties of the product, including its caloric value and water-holding capacity, can be changed by varying the degree of modification at either step, e.g., the degree of retrogradation and/or degree of hydrolysis.

The retrogradation step of the present process involves incubating the starch in an aqueous solution at elevated temperatures followed by another incubation at lower temperatures, thereby causing the formation of crystalline regions in the starch molecule. The retrograded starch produced after this step can be used, as is, as a bulking agent or extender for foods, or as a tabletting aid. Alternatively, the retrogradation step can then be followed by either enzymatic hydrolysis catalyzed by a glycosidase, or a mixture of glycosidases or by acid-catalyzed hydrolysis, to yield a water-insoluble low-calorie starch product.

The present product is a food grade, aqueous insoluble starch product which is useful as a low-calorie bulking agent for foods. The product has a number of advantages over traditional bulking agents. The product has few calories, and its physical properties can be easily modified for a given application by controlling the degree of retrogradation and the amount of amorphous material which remains linked to the crystalline starch. Due to the product's increased functionality, it has a variety of applications in carbohydrate- and fat-based foods. For example the retrograded and/or enzyme modified starch product can be used as a sugar and/or flour substitute in a variety of baked products and also as a bulking agent in low-fat food formulations, such as low-calorie, low-fat margarines and mayonnaise.

DETAILED DESCRIPTION OF THE INVENTION

The present invention relates to a process for modifying starch to produce a retrograded starch product useful in many food applications. In the first step, starch is subjected to retrogradation During this step it undergoes a physical transition that results in a new structure in which crystalline, double-helical regions (retrograded regions) interspersed with amorphous regions. The retrograded starch produced after this step can be used as a bulking agent, extender, or substitute for sugar, flour or fat in foods or as a tabletting aid, or can be further modified by hydrolysis of the non-crystalline or amorphous regions. In the hydrolysis step this product is treated with an appropriate glycosidase, or a mixture thereof, or an acid to hydrolyze the amorphous regions, while leaving the crystalline regions intact. The resulting product is a crystalline starch which has a low degree of amorphous starch regions. That is, the material is constituted mostly of retrograded crystalline starch. Preferably, less than about 10% by weight of the product will be amorphous starch regions. The structure of the final material, and/or its functional properties, depends in part on the enzyme specificity and the degree of hydrolysis. Thus the amount of amorphous material which remains attached to the crystalline regions can be controlled by the choice of glycosidase enzyme, and by controlling the conditions of the enzyme-mediated or acid-mediated hydrolysis step.

Polysaccharides which are useful as starting material in this process are starches from a number of sources (e.g., corn, wheat, oats, potato) as well as amylose, dextrans, glycogens and galactomannans. Polysaccharides consisting of linear chains of amylose molecules and branched chains of amylopectin molecules, which are generally derived from plant sources can be used. For example, starch can be derived from corn, wheat, rice, potatoes, topioca, cassava or arrow-root, alant, amioca or sago.

The first step of the process is performed by dispersing a starch sample in an aqueous medium, such as water, or a buffer or a mixture of water and an organic solvent (e g., DMSO) containing at least 80% by volume of water. This process can be simplified by dissolving the sample first in an appropriate organic solvent (DMSO, for example) and then diluting it with water. The suspension generally contains from about up to about 10% (w/v) of starch. The dispersion is then incubated at an elevated temperature preferably about 60°–120° C. for a period of time sufficient to cause retrogradation to occur (e.g., about 5 to about 10 hours). The product is then cooled and incubated at a lower temperature (about 4°–20° C.) for about 0.5 to about 4 days. At this point, at least 90% (by weight) of the starch consists of crystalline regions.

Since the retrogradation of amylose is retarded by the presence of amylopectin in the starch, the first step of process can be accelerated by enzymatic conversion of the amylopectin to amylose prior to retrogradation. The conversion can be accomplished by the use of debranching enzymes such as pullulanase or isoamylase. Partial hydrolysis of the polysaccharide chain with (1-4)specific glycosidase (e g., alpha amylase) is useful for this purpose.

The retrograded polysaccharide produced in the first step of the present process is then subjected to hydrolysis to reduce or eliminate the amorphous regions. Hydrolysis can be accomplished enzymatically (e.g., using a glycosidase) or chemically (e.g., using an acid). This step is generally carried out in a stirred tank reactor. A glycosidase enzyme a mixture of thereof, or an acid is added to a suspension of the retrograded polysaccharide in an aqueous medium, e.g., water or a buffer and the reaction mixture is incubated with stirring until the desired degree of hydrolysis is achieved, generally from about 1 to 30 hours. The amount of enzyme added will vary, depending upon the enzyme or enzyme mixture used. the activity of the enzyme and the process conditions (e.g., time, temperature). The amount will generally be sufficient to complete hydrolysis of the non-crystalline regions in less than about 30 hours. Acids which can be used in the hydrolysis step are acids generally used to hydrolyze carbohydrates, which include mineral acids such as HCl, $H_2SO_4$ and TFA (trifluoroacetic acid). Concentrations of acid used is generally about 0.2N. Higher concentrations can be used but generally do not result in faster hydrolysis.

The temperature of the reaction mixture can range from about 10° C. to about 80° C. The resulting residue is washed to remove the enzymes or acids and the water-soluble sugars and oligosaccharides which are the by-products of the reaction, and the resulting water-insoluble product is dried. Drying can be accomplished, for example, by stripping the residual amount of water with a water-miscible organic solvent such as acetone, by air-drying or freeze drying.

A variety of different enzymes can be used in the second step of the present process. The enzyme is selected on the basis of the chemical structure of the starting material. For example, if amylose that consists of alpha-D-glucopyranose residues joined by (1-4) bonds, is the starting material, then an enzyme specific for (1-4) glucosidic linkages, such as alpha amylase, is employed. For starches that contain both (1-4) and (1-6) linkages, either a mixture of (1-4)- and (1-6)-specific glycosidases, or one enzyme specific for both (1-4) and (1-6) linkages is used. For example, a combination of a (1-4) specific alpha amylase and (1-6) specific pullulanase or isoamylase can be used. Alternatively, amyloglucosidase, which is (1-4) and (1-6) specific, can be used alone.

Glycosidases which are employed as catalysts in the present process should exhibit high operational stability (e.g., can be reused without a significant loss of enzymatic activity for at least 50 hours) and should efficiently catalyze the hydrolysis of glycosidic bonds. It is important to consider that while none of known alpha amylases can hydrolyze D-glycosidic bonds in close proximity to crystalline regions because of their binding site requirements, their specificity towards the amorphous regions varies significantly. Human-salivary and porcine pancreatic alpha amylase for example, leave five D-glucopyranose residues adjacent to the crystalline region unhydrolyzed. *Bacillus subtilis* (*B. subtilis*) alpha amylase leaves nine D-glucopyranose residues untouched. Jane and Robyt, *Carbohydrate Research*, 132:105 (1984). If a higher degree of hydrolysis is required, for example, a combination of one of the above enzymes with amyloglucosidase can be used.

Acids which can be used in the second step of the process include acids capable of hydrolyzing glycosidic bonds, such as HCl, $H_2SO_4$ and TFA.

The modified product produced by the present process is a predominantly crystalline, retrograded starch having a small amount of amorphous regions. The product has many desirable properties. For example the retrograded starch or hydrolyzed retrograded starch produced by the present process meets the requirements for the category of dietary fibers, and can be classified as natural, since no chemical alteration other than hydrolysis of the naturally-occurring starch starting material occurs. The product has a microcrystalline structure and a wide range of water-holding capacities and digestibility. It can be used as a dietary fiber supplement, as a replacement or substitute for sugar and flour in a variety of baked goods, as a fat extender in low-fat formulations as a tablet ting aid and as an inhibitor of excessive ice crystal formation.

The retrograded, modified starch of the present invention is particularly useful in formulating foods containing reduced amounts of sugar, flour or fat. Foods formulated using the retrograded starch in place of sugar, flour and/or fat have a lower calorie content, a higher fiber content and, if fat is the ingredient replaced, a lower fat content. Foods which can be formulated using the present retrograded starch products include cookies, fudge, brownies, low-fat margarine spreads and frozen desserts. The amount of sugar, flour or fat in a given formulation which can be replaced by the retrograded starch product will depend in part upon the formulation, the desired properties of the food and the amount of calorie and/or fat reduction desired. Retrograded starch also can be added as an extender to a formulation without reducing any of the other ingredients. The extended product has a lower calorie or fat content per volume compared to the unextended product.

The invention is further illustrated by the following Examples.

EXAMPLES

Materials

Amylose dextran standards alpha amylase (EC 3.2.1.1) from *B. subtilis* and porcine pancreas (pancretin), and amyloglucosidase (EC 3.2.1.3) from *Aspergillus niger* (*A. niger*) with specific activities of 136 IU/mg, 7800 IU/ml and 350 IU/ml, respectively, were purchased from Sigma Chemical Company (St Louis, Mo.) HT-concentrated alpha. amylase was obtained from Miles Laboratories (Elkhart, Ind.). High amylose starch (Amylomaize VII) was obtained from American Maize-Products Co. (Hammond, Ind.). DMSO was purchased from Aldrich Chemical Company (Milwaukee, Wis.).

Methods

Alpha Amylase Assay

The activity of alpha amylase was determined in the hydrolysis of starch by following the appearance of the reducing sugars. Alpha amylase (0.1–0.7 IU) was added to 2 ml 2% solution of soluble starch in 20 mM potassium phosphate buffer pH 6.9 containing 5 mM NaCl and 1 mM $CaCl_2$. The solution was incubated at 37° C. Periodically, 10 μl samples were withdrawn and analyzed for reducing sugars following the standard Somoygi-Nelson procedure Nelson, N., *J. Biol. Chemistry*, 153:375 (1944).

Amyloglucosidase Assay

The activity of amyloglucosidase was determined in a way similar to that of alpha amylase. Amyloglucosidase (0.1 IU) was added to a 2% solution of starch in 0.1M NaOAc pH 4.5 The solution was incubated at 37° C. Periodically 10 μl samples were withdrawn and analyzed for reducing sugars following the procedure of Somoygi-Nelson.

Water-Holding Capacity Measurements

Five hundred milligrams of the sample were suspended in 5.0 g water. The suspension was mixed on a Vortex mixer and then shaken on an orbit shaker at 200 rpm at 20° C. for 15 minutes. It was followed by centrifugation at 3000 g for 20 minutes at 20° C. The aqueous phase was removed and the precipitate was then weighed. The water holding capacity (WHC) was calculated by dividing the weight of bound water by the weight of the dry sample.

Retrogradation of Amylose

Twenty five grams of amylose was dissolved in 250 ml DMSO while heating and 2250 ml of water was then slowly added. The resultant solution was stirred at 80° C. for 1 hour and then left at 4° C. for 15 hours. The solid precipitate formed as a result of the incubation was isolated by centrifuging at 9000 g for 20 minutes. The precipitate was then washed 3 times with water (500 ml) and lyophilized.

Retrogradation of Starch

Fifteen hundred g of high amylose starch was suspended in 4 L of water to make a smooth, homogenous slurry. This slurry was added to 26 L of boiling (autoclaved) water with constant stirring. The resulting suspension was autoclaved at 121° C. for 8 hours The solution was cooled and incubated at 24° C. for 16 hours and then at 8° C. for another 48 hours. Retrograded amylose precipitated during this process was removed from the suspension by continuous centrifugation and subjected to enzymatic hydrolysis.

When enzymatic modification was not required the solid retrograded amylose was washed five times with anhydrous acetone and then once with anhydrous ethanol. The final solid was dried at 40° C. for 10 hours under vacuum. The process yielded 1 kg of retrograded starch.

Enzymatic Hydrolysis of Retrograded Amylose

A suspension was prepared by adding 45 g of retrograded amylose, prepared as described above, to 500 ml of 50 mM sodium acetate buffer (pH 5.5) containing 1.0 mM $CaCl_2$ and 5 mM NaCl. Alpha amylase from porcine pancreas (30 mg) and 2 ml (18 mg) of amyloglucosidase were added to the suspension. The reaction flask was placed on a shaker at 225 rpm and incubated for 18 hours at 50° C. The unhydrolyzed solid material was recovered by centrifugation (20 minutes at 9000 g), washed three times with water and lyophilized.

Enzymatic Hydrolysis of Retrograded Starch

A suspension was prepared by adding 10 g of HT-concentrated alpha-amylase to 200 mL of water with stirring for 4 hours. The resulting dark brown solution was centrifuged and filtered. The supernatant was decanted and saved. The precipitate was washed twice with 50 mL water, centrifuged and added to the supernatant, yielding 350,000 IU of amylase activity.

Human salivary amylase was prepared by the following procedure: One hundred and thirty mL of human saliva was collected, centrifuged, and filtered yielding 130,000 IU of human salivary amylase activity.

One kg of retrograded starch prepared as described above was suspended in 10 L of water with stirring to form a smooth, homogenous suspension. Both of the amylase solutions were then added and the reaction mixture was stirred at 24° C. for 25 hours. The resulting enzyme-modified retrograded starch (EMRS) was removed from the suspension by continuous centrifugation. The solid was dispersed in water to form a 12% (w/w/) suspension and freeze-dried.

Determination of Digestibility

A solution containing 2 5% high amylose starch in 500 mM phosphate buffer (pH 7 5) was prepared. To 1 ml of this solution. 1 ml of pancretin solution (10 mg/ml) was added. The mixture was incubated at 37° C. for 30 minutes. Periodically 0.1 ml aliquots were removed, and 0.1 ml of an amyloglucosidase solution (15 IU/ml) in 50 mM NaOAc buffer (pH 5.0) was added. The solution was incubated at 37° C. for 30 minutes and the reducing sugars formed were determined using the Somoygi-Nelson method.

Evaluation of Particle Size

The particle size of the starch product was determined using a Microtrac particle size analyzer (Leeds & Northrup Instruments, North Wales, Pa.) following the manufacturer's instructions.

Molecular Weight Determination

The average molecular weight of the starch product was determined by HPLC. A Perkin Elmer Series 400 HPLC (Perkin Elmer Corp., Norwalk Conn.) interfaced to a Kaypro 286i data collection system (Kaypro Corp., Solana Beach, Calif.) was used. A BioRad (BioRad, Richomd, Calif.) TSK-250 column (600×7.5 mm) with a Waters (Waters Associates, Milford, Mass.) Differential Refractometer Series 403 detector was used to determine the average molecular weight of the starch samples. The column was calibrated using commercially available dextran standards. The column was eluted with 15% DMSO in 250 mM NaOAc pH 4.0 at a flow rate of 0.6 ml/min. One hundred microliters of a 10 mg/ml solution was injected for the determination of the molecular weight.

Tableting

Tablets were formed by placing 500 mg of enzyme-modified retrograded starch into a tablet die, and compressing at 3.9 ton/cm² for 5 minutes at 20° C. on a Carver Laboratory Press (F. S. Carver Inc., Menomonee Falls, Wis.).

EXAMPLES

Example 1

Twenty five grams of amylose were dissolved in 50 ml of DMSO and retrograded as described in the Methods section. Fifteen grams of crystalline white, water-insoluble material was obtained (yield, 60%). Retrograded amylose (RA) was then hydrolyzed enzymatically with a mixture of alpha amylase and amyloglucosidase as described in Methods. The hydrolysis of forty five grams of RA resulted in twenty nine grams of crystalline water-insoluble enzyme-modified retrograde amylose (EMRA).

Particle size distribution, water-holding capacity, digestibility and average molecular weight of RA and EMRA was then evaluated as described above.

The average particle size was determined by forming a dilute suspension of the material in water at room temperature and measuring the size distribution on the Microtrac Small Particle Analyzer. It was found that the EMRA is composed of small crystalline particles with a median volume diameter of 6.6 μ (80% of the particles were between 2.5 and 11.8 μ).

The digestibility of RA and EMRA was then determined and compared with that of the soluble starch. Soluble starch was completely digested in 30 minutes. On the other hand, RA and EMRA were 50% and 7.8% digested, respectively in 30 minutes. No further degradation was detected up to 2 hours. The results indicate that both RA and EMRA are much more resistant to hydrolysis than the starting material.

Molecular weight was determined by HPLC and analysis revealed that the average molecular weight of RA is more than 70,000 daltons and that of EMRA is about 9000 daltons.

The results indicated that an exhaustive hydrolysis takes place resulting in the formation of oligomers with an average degree of polymerization of 50.

The water holding capacity of amylose was found to be 6.4 g/g. Retrogradation, and enzymatic treatment resulted in a decreased level of water holding capacity. Water-holding capacity for RA and EMRA was found to be 3.4 g/g and 2.0 g/g respectively.

Example 2

Amylose was retrograded and enzymatically modified as described above and evaluated as an ingredient in a hard sugar cookie.

| | | EXPERIMENTAL | |
|---|---|---|---|
| INGREDIENT | CONTROL | 1 | 2 |
| Flour | 40.50 | 40.50 | 13.12 |
| Creamtex-partially hydrogenated vegetable oil | 19.30 | 19.30 | 25.03 |
| Brown sugar | 14.40 | — | 18.67 |
| Granulated sugar | 14.40 | 14.40 | 18.67 |
| Whole egg solids | 2.30 | 2.30 | 3.00 |
| Water | 7.40 | 20.15 | 9.60 |
| Salt | 0.60 | 0.60 | 0.78 |
| Baking soda | 0.60 | 0.60 | 0.78 |
| Vanilla extract | 0.50 | 0.50 | 0.65 |
| EMRA | — | 7.50 | 9.70 |

FORMULATION AND PREPARATION PROCEDURE FOR HARD SUGAR COOKIES

Preparation Procedure:
1. The eggs were hydrated in water (2.3 g egg solids to 7.4 g water).
2. Salt, sugar, baking soda and creamtex were creamed.
3. The hydrated eggs were added slowly and mixed well.
4. The remaining dry ingredients were added, and mixed for approximately 30 seconds.
5. The vanilla and remaining water were added and mixed well.
6. 15 g were placed on ungreased baking sheet and baked at 375° F. about 8 minutes.

Recipe
Source: ABIC International Consultants, Incorporated.

In experimental formula 1, EMRA was used to replace all the brown sugar in the formula. The resultant cookie was somewhat gritty, but was a generally acceptable product. Formula 2 contains 9.7% of EMRA, reduced flour (30% of the control) and an increased amount of sugar. The resulting product was a hard cookie with highly acceptable texture.

Example 3

High amylose starch retrograded as described above was evaluated as ingredient in microwavable fudge.

FORMULATION AND PREPARATION PROCEDURE FOR MICROWAVABLE FUDGE

| INGREDIENTS | Weight Percent | |
|---|---|---|
| | CONTROL | EXPERIMENTAL |
| confectioner's sugar (10x) | 68.30 | 34.15 |
| cocoa powder (unsweetened) | 7.00 | 7.00 |
| whole milk | 7.30 | 21.00 |
| pure vanilla extract | 1.10 | 1.10 |
| sweet cream butter | 16.30 | 16.30 |
| retrograded starch (RS) | 0.00 | 20.45 |

Preparation Procedure:
1. A dry blend of the sugar, cocoa powder and starch was prepared.
2. Milk, butter and vanilla were added to the dry blend.
3. The mixture was placed in a microwave and cooked on a high setting for two (2) to four (4) minutes to melt the butter.
4. The mixture was stirred to thoroughly disperse the melted butter and milk.
5. The resulting mixture was chilled in a refrigerator to set.

Half of the amount of confectioner's sugar in the recipe was substituted with EMRA and whole milk. The sugar-reduced fudge was darker in color and exhibited a richer, almost brownie-like, texture compared to the control. Final texture of the sugar reduced product could be altered simply by changing the ratio of milk to starch (decreasing starch and increasing milk will give a chewy, wetter finished product). Although the sweetness of the sugar-reduced product was lower than that of the control, the addition of aspartame at 0.15 per cent will give a product with similar sweetness.

Example 4

Amylose was retrograded as described above and evaluated as ingredient in 30% fat margarine.

FORMULATION AND PREPARATION PROCEDURE FOR LOW FAT MARGARINE

| 30% FAT MARGARINE INGREDIENTS | CONTROL | EXPERIMENTAL WEIGHT PERCENT | |
|---|---|---|---|
| | | 1 | 2 |
| Oil Phase | | | |
| Margarine oil | 28 | 28 | 28 |
| Campul GMO (Capital City Products) (mono and di-glycerides) | 2 | 2 | 2 |
| Lecithin | 0.2 | 0.2 | 0.2 |
| Artificial butter flavor (Givaudan) | 0.05 | 0.05 | 0.05 |
| Beta-carotene dispersion (1%) | 0.05 | 0.05 | 0.05 |
| Water Phase | | | |
| Water | 69 | 61.5 | 61.5 |
| Retrograded amylose | — | — | 7.5 |
| Paselli SA2 (Avebe) | — | 7.5 | — |
| Morton salt | 1 | 1 | 1 |
| Chris Hansen starter distillate 15x | 0.01 | 0.01 | 0.01 |
| Alex Fries artificial cream flavor | 0.01 | 0.01 | 0.01 |

*Cargill 270 (SFI 2.5 maximum) 50% + Cargill 357 (SFI 4.0) 50%

Preparation Procedure

-continued

FORMULATION AND PREPARATION PROCEDURE FOR LOW FAT MARGARINE

1. The oil was warmed to about 55° C.
2. The water phase was warmed to about 85° C. for 30 minutes, then cooled to 55° C.
3. The phases were blended for 2 minutes in a Waring blender.
4. The emulsion was allowed to solidify by placing at 4° C. for 18 hours.

The control which contained no stabilizers, did not form a stable product. The emulsion broke before the product was cooled. Experimental formula 1, prepared with Paselli SA2 (dextran-based commercially available product) first formed a stable emulsion that broke on cooling. The margarine prepared with retrograded starch Experimental (formula 2) formed a stable product that was homogenous and did not break on cooling. On storage at room temperature for 18 hours there was some water leakage.

Example 5

High amylose starch was retrograded and enzymatically modified as described above and evaluated as ingredient in reduced-flour brownies.

FORMULATION AND PREPARATION PROCEDURE FOR REDUCED-FLOUR BROWNIES

| INGREDIENTS | WEIGHT PERCENT | |
|---|---|---|
| | CONTROL | EXPERIMENTAL |
| shortening | 16.00 | 16.00 |
| granulated sugar (sucrose) | 36.47 | 36.47 |
| eggs | 16.75 | 16.75 |
| unsweetened chocolate squares | 10.55 | 10.55 |
| baking powder | 0.24 | 0.24 |
| salt (NaCl) | 0.57 | 0.57 |
| pure vanilla extract | 1.00 | 1.00 |
| all-purpose flour | 18.42 | 9.41 |
| EMRS | — | 9.41 |
| TOTAL | 100.00 | 100 |

Preparation Procedure
1. The shortening and chocolate were melted together with constant stirring over very low heat.
2. This mixture was set aside to cool.
3. Eggs were beaten until light then blended into the sugar.
4. Cooled chocolate/shortening liquid was slowly beaten into the sugar/egg mixture along with the vanilla.
5. All dry ingredients (sugar, flour, starch, baking powder and salt) were slowly blended into the aforementioned mixture.

Brownies were formulated, baked for 35 minutes and compared with the control. Brownies containing EMRS exhibited a slightly chewier and drier texture compared to the control. They formed a generally acceptable produce with acceptable texture and good organoleptic properties.

Example 6

High amylose starch was retrograded and enzymatically modified as described above and evaluated as ingredient in reduced-flour sugar cookies.

| FORMULATION AND PREPARATION PROCEDURE FOR REDUCED-FLOUR SUGAR COOKIES | | |
|---|---|---|
| | WEIGHT PERCENT | |
| INGREDIENTS | CONTROL | SAMPLE |
| shortening | 21.00 | 21.00 |
| granulated sugar (sucrose) | 23.92 | 23.92 |
| fresh egg | 7.32 | 7.32 |
| whole pasteurized milk | 3.47 | 3.47 |
| baking powder | 0.65 | 0.65 |
| salt (NaCl) | 0.24 | 0.24 |
| pure vanilla extract | 0.44 | 0.44 |
| all-purpose flour | 42.96 | 24.48 |
| EMRS | — | 24.48 |
| TOTAL | 100.00 | 100.00 |

Preparation Procedure
1. The shortening, sugar and vanilla were creamed together in a mixing bowl
2. The egg was then added to the creamed mixture and beaten until mixture was light and fluffy. The milk was subsequently stirred in.
3. All the dry ingredients (sugar, flour, baking powder, salt and starch) were first blended together and then sifted and mixed into the creamed mixture.
4. Finished dough was chilled for one hour before baking.
5. Cookies were cut or rolled into desired shapes and placed on a greased cookie sheet at 375° F. for six to eight minutes.

Cookies were formulated and baked on a greased sheet for 35 minutes. The test samples exhibited a slightly chewier texture compared control, however product was acceptable and generally comparable in organoleptic properties to the control.

Example 7

High amylose starch was retrograded and enzymatically modified as described in the "Methods". It was evaluated as ingredient in non-fat frozen dairy dessert.

| FORMULATION AND PREPARATION PROCEDURE FOR NON-FAT FROZEN DAIRY DESSERT | | |
|---|---|---|
| | Weight Percent | |
| INGREDIENTS | CONTROL | SAMPLE |
| pasteurized skim milk | 70.808 | 68.308 |
| granulated sugar (sucrose) | 18.000 | 18.000 |
| non-fat dry milk (NFDM) | 6.800 | 6.800 |
| unsweetened cocoa powder | 3.600 | 3.600 |
| EMRS | 0.000 | 2.500 |
| stabilizer (Germantown Pioneer) | 0.750 | 0.750 |
| salt (NaCl) | 0.030 | 0.030 |
| cream flavor | 0.010 | 0.010 |
| TOTAL | 100.000 | 100.000 |

Preparation Procedure
1. The dry ingredients (sugar, cocoa powder, NFDM, stabilizer gum blend, modified starch and salt) were blended together.
2. The liquid ingredients (milk, vanilla and cream flavor) were then blended in a Waring blender.
3. With blender on low speed, the dry blend was slowly added to the liquid mix.
4. Once all dries were added, the mixture was blended for an additional five minutes or until mix was smooth and homogenous.
5. The mix was then chilled to 4° C. Freezing was accomplished with a Gelatiera Gaggia (batch type) ice cream freezer. The product was processed for 20-30 minutes until a 60-70 per center over run was achieved.
6. Finished product was aged at 4° C. for at least 48 hours before evaluation.

An acceptable frozen dessert was obtained with the modified starch sample. The starch sample had a fuller mouthfeel and less ice crystal formation compared to the control.

Example 8

One and one half kilograms of high amylose starch were suspended in 4 L of water and retrograded as described in the Methods section One kg of white, water-insoluble material was obtained (yield: about 67%). Retrograded starch (RS) was then hydrolyzed enzymatically with the mixture of alpha amylases. The hydrolysis of 1 Kg of RS resulted in 760 g of enzyme-modified retrograded starch (EMRS; yield: about 76%).

Particle size distribution, water-holding capacity and digestibility were then evaluated. The average particle size of the EMRS was determined by the same method as that for EMRA. It was found that EMRS is composed of small particles having a median volume diameter of 9.75 $\mu$ (80% of all particles having a diameter between 4.2 and 20.7 $\mu$).

The digestibility of RS and EMRS was found to be 63% and 32% respectively. The results indicate that alpha amylases are only capable of carrying out a partial hydrolysis of RS. The water-holding capacity of RS and EMRS was found to be 3.5 g/g and 2.4 g/g, respectively.

Example 9

High amylose starch was retrograded and enzymatically modified as described above. The retrograded starch was evaluated as a tableting aid. Two 500 mg tablets were made as described in the Methods section. Tablets having an acceptable appearance, color and texture were formed. The dispersibility of the tablets was determined by placing a tablet in a 125 ml flasks containing 50 ml of phosphate buffer (pH 7.0) and a 125 ml flask containing 50 ml of citrate buffer (pH 3.0). The flasks were placed on a shaker and incubated at about 200 rpm at 37° C. The tablets dispersed completely in both buffers within 5 minutes, which is consistent with a desirable dispersion rate for tablets used in human and animal pharmaceuticals.

Equivalents

Those skilled in the art will recognize or be able to ascertain using no more than routine experimentation, many equivalents to the specific embodiments of the invention described specifically herein. Such equivalents are intended to be encompassed in the scope of the following claims.

We claim:

1. A food product containing a food-grade water insoluble material comprising water-soluble crystalline starch microparticles which are substantially free of amorphous regions.

2. A reduced calorie food product wherein at least a portion of the sugar or flour has been replaced by a food-grade water-insoluble material comprising water-insoluble crystalline starch microparticles which are substantially free of amorphous regions.

3. A reduced-fat product wherein at least a portion of the fat has been replaced by a food-grade water-insoluble material comprising water-insoluble crystalline starch microparticles which are substantially free of amorphous regions.

4. A food produce containing a food-grade water-insoluble crystalline starch microparticles produced by a method comprising the steps of:
   a. incubating a starch dispersion under conditions sufficient for crystallization of at least a portion of the starch to occur;
   b. incubating a suspension of the crystalline starch formed in (a) with a catalyst under conditions sufficient for hydrolysis of the amorphous regions to occur; and
   c. washing the starch with water to remove the catalyst and water-soluble by-products.

5. The food product of claim 4 wherein the starch is selected from the group consisting of: amylomaize starch, corn starch, wheat starch, oat starch and potato starch and amylose.

6. The food product of claim 4 wherein the catalyst of step (b) is one or more glycosidase enzymes.

7. The food product of claim 6 wherein the glycosidase is selected from the group consisting of: alpha amylase, pullulanase, isoamylase and amyloglycosidase.

8. The food product of claim 4 wherein the catalyst of step (b) is an acid.

9. The food product of claim 8 wherein the acid is selected from the group consisting of: HCl, $H_2SO_4$ and TFA.

10. The food product of claim 4 comprising cookies, frosting, brownies, margarine, fudge, chocolate syrup or frozen desserts.

* * * * *

UNITED STATES PATENT AND TRADEMARK OFFICE
CERTIFICATE OF CORRECTION

PATENT NO. : 5,051,271

DATED : September 24, 1991

INVENTOR(S) : Radha Iyengar, Aleksey Zaks and Akiva Gross

It is certified that error appears in the above-identified patent and that said Letters Patent is hereby corrected as shown below:

Claim 4, column 13, line 1, change "produce" to ---product---

Signed and Sealed this

Twelfth Day of January, 1993

*Attest:*

DOUGLAS B. COMER

*Attesting Officer*     Acting Commissioner of Patents and Trademarks

UNITED STATES PATENT AND TRADEMARK OFFICE
CERTIFICATE OF CORRECTION

PATENT NO. : 5,051,271
DATED : September 24, 1991
INVENTOR(S) : Radha Iyengar, Aleksey Zaks and Akiva Gross It is certified that error appears in the above-identified patent and that said Letters Patent is hereby corrected as shown below:

<u>Col. 12</u>

Claim 1, line 56, delete "water-soluble" and insert ---water-insoluble---.

Signed and Sealed this

Twenty-first Day of September, 1993

Attest:

BRUCE LEHMAN

*Attesting Officer*     *Commissioner of Patents and Trademarks*